(12) United States Patent
Clader et al.

(10) Patent No.: US 6,294,554 B1
(45) Date of Patent: Sep. 25, 2001

(54) MUSCARINIC ANTAGONISTS

(75) Inventors: John W. Clader, Cranford; Joseph A. Kozlowski, Princeton; Stuart W. McCombie, Caldwell; Michael W. Miller, Westfield; Susan F. Vice, Mountainside, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/651,652

(22) Filed: Aug. 30, 2000

Related U.S. Application Data

(60) Provisional application No. 60/155,352, filed on Sep. 22, 1999.

(51) Int. Cl.[7] ................ A61K 31/445; C07D 401/04; C07D 405/14
(52) U.S. Cl. .................... 514/316; 546/187; 546/189
(58) Field of Search ................ 514/316; 546/189, 546/187

(56) References Cited

FOREIGN PATENT DOCUMENTS

| | | |
|---|---|---|
| 96/26196 | 8/1996 | (WO) . |
| 98/05292 | 2/1998 | (WO) . |
| 00/00488 | 1/2000 | (WO) . |

OTHER PUBLICATIONS

Melchiorre et al, *J. Med. Chem.*, 36 (1993), p. 3734–3737.
Baumgold et al, *Eur. J. Pharmacol.*, 251 (1994), p. 315–317.
Cheng et al, *Biochem. Pharmacol.*, 22 (1973), p. 3099–3108.

*Primary Examiner*—Charanjit S. Aulakh
(74) *Attorney, Agent, or Firm*—Anita W. Magatti

(57) ABSTRACT

Amide derivatives of 1,4 di-substituted piperidine compounds of the formula

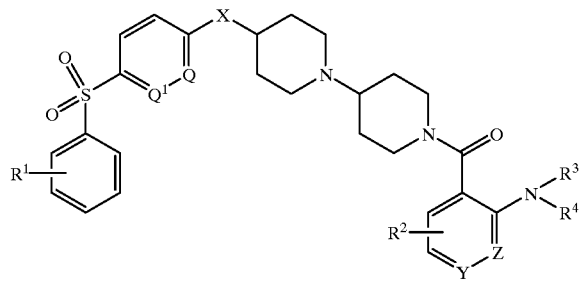

or a pharmaceutically acceptable salt, ester or solvate thereof, wherein Q and $Q^1$ are each —CH=, or one of Q and $Q^1$ is —CH= and the other is —N=;

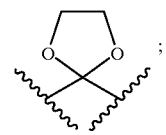

X is —$CH_2$— or

Y and Z are —$C(R^5)$=, or one of Y and Z is —$C(R^5)$= and the other is —N=;

$R^1$ is 1 to 3 substituents selected from H, halogen and alkoxy;

$R^2$ and $R^5$ are 1 to 3 substituents selected from H, halogen, alkyl and alkoxy; and $R^3$ and $R^4$ are H or $(C_1-C_6)$alkyl are muscarinic antagonists useful for treating cognitive disorders such as Alzheimer's disease. Pharmaceutical compositions and methods of preparation are also disclosed.

18 Claims, No Drawings

MUSCARINIC ANTAGONISTS

CROSS REFERENCE TO RELATED APPLICATIONS

This application claims the benefit of U.S. Provisional Application No. 60/155,352, filed Sep. 22, 1999.

BACKGROUND OF THE INVENTION

The present invention relates to amide derivatives of 1,4-di-substituted piperidines useful in the treatment of cognitive disorders, pharmaceutical compositions containing the compounds, methods of treatment using the compounds, and to the use of said compounds in combination with acetylcholinesterase inhibitors.

Alzheimer's disease and other cognitive disorders have received much attention lately, yet treatments for these diseases have not been very successful. According to Melchiorre et al. (J. Med. Chem. (1993), 36, 3734–3737), compounds that selectively antagonize M2 muscarinic receptors, especially in relation to M1 muscarinic receptors, should possess activity against cognitive disorders. Baumgold et al. (Eur. J. of Pharmacol., 251, (1994) 315–317) disclose 3-α-chloroimperialine as a highly selective m2 muscarinic antagonist.

Piperidine-derivative muscarinic antagonists useful in the treatment of cognitive disorders such as Alzheimer's disease are disclosed in WO96/26196 and WO98/05292. In particular, WO98/05292 discloses compounds of the generic formula

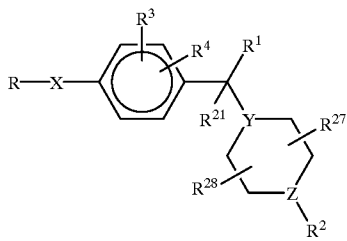

wherein, inter alia, Y is CH; Z is N; X is —SO$_2$—; R is substituted phenyl; R$^1$ and R$^{21}$ are each H, or together form an ethylenedioxy group; R$^3$, R$^4$, R$^{26}$ and R$^{27}$ are hydrogen; and R$^2$ is a N-substituted 4-piperidine derivative, wherein the N-substituent can be an amino-substituted benzoyl or pyridinecarboxyl group. Similar compounds wherein the benzene ring is replaced by a pyridinyl ring are disclosed in PCT/US99/12821. Compounds of the present invention represent a selection invention over WO98105292 and PCT/US99/12821.

SUMMARY OF THE INVENTION

The present invention relates to compounds of the structural formula I

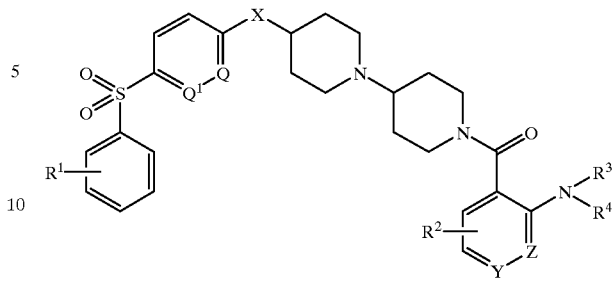

or a pharmaceutically acceptable salt, ester or solvate thereof, wherein

Q and Q$^1$ are each —CH=, or one of Q and Q$^1$ is —CH= and the other is —N=;

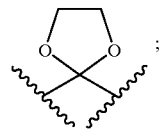

X is —CH$_2$— or

Y and Z are independently selected from the group consisting of —C(R$^5$)=, or one of Y and Z is —C(R$^5$)= and the other is —N=;

R$^1$ is 1 to 3 substituent independently selected from the group consisting of H, halogen and (C$_1$–C$_6$)allkoxy;

R$^2$ and R$^5$ are independently 1 to 3 substituents independently selected from the group consisting of H. halogen, (C$_1$–C$_6$)alkyl and (C$_1$–C$_6$)alkoxy; and R$^3$ and R$^4$ are independently selected from the group consisting of H and (C$_1$–C$_6$)alkyl.

One group of preferred compounds is that wherein both Y and Z are —C(R$^5$)=, wherein R$^5$ is preferably H, methyl or halogen, Also preferred are compounds wherein Y is —CH=, Z is —N= and R$^2$ is hydrogen.

R$^1$ is preferably halogen, more preferably chloro, or methoxy. In particular, R$^1$ is 3-chloro or 4-methoxy.

Q and Q$^1$ are preferably each —CH=.

Preferred R$^2$ substituents are Cl, F and methyl; 3-methyl is more preferred.

R$^3$ and R$^4$ are preferably each H.

Compared to the compounds specifically disclosed in WO98/05292 or PCT/US99112821, none of which contain the 2-amino-benzamide (i.e., anthranilamide) or the 2-aminopyridincarboxamide moiety, compounds of the present invention show surprisingly greater selectivity for the m2 receptor, and also show improved oral absorption and in vivo efficacy.

In another aspect, the invention relates to a pharmaceutical composition comprising a therapeutically effective amount of a compound of formula I in a pharmaceutically acceptable carrier. The invention also relates to a method of using a compound of formula I or a pharmaceutical composition comprising a compound of formula I in the treatment of a cognitive disease or neurodegenerative disease comprising administering an effective amount of a compound or composition of this invention to a mammal in need of such treatment.

In still another aspect, the invention relates to a method for treating a cognitive disease or neurodegenerative disease comprising administering to a mammal in need of such treatment an effective amount of a combination of a compound of formula I and an acetylcholinesterase inhibitor.

In a final aspect, the invention relates to a kit for treating a cognitive disease or neurodegenerative disease comprising in separate containers in a single package pharmaceutical compositions for use in combination, in one container a compound of formula I in a pharmaceutically acceptable carrier and in a second container, an acetylcholinesterase inhibitor in a pharmaceutically acceptable carrier, the combined quantities being an effective amount.

DETAILED DESCRIPTION

As used herein, halogen represents fluoro, chloro, bromo or iodo.

When a variable appears more than once in the structural formula, for example when $R^1$ is two or three substituents, the identity of each variable appearing more than once may be independently selected from the definitions for that variable.

Compounds of formula I can exist in unsolvated as well as solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compounds of formula I can be prepared using methods well known to those skilled in the art, for example by procedures disclosed in WO98/05292. The skilled artisan will recognize that other procedures may be applicable, and that the procedures may be suitably modified to prepare other compounds within the scope of formula I.

Compounds of formula I as defined above are preferably prepared as shown in the following reaction schemes (abbreviations used in the schemes and descriptions are defined below). In general, compounds of formula I are prepared by coupling an amine of formula II with an anthranilic or nicotinic acid of formula III:

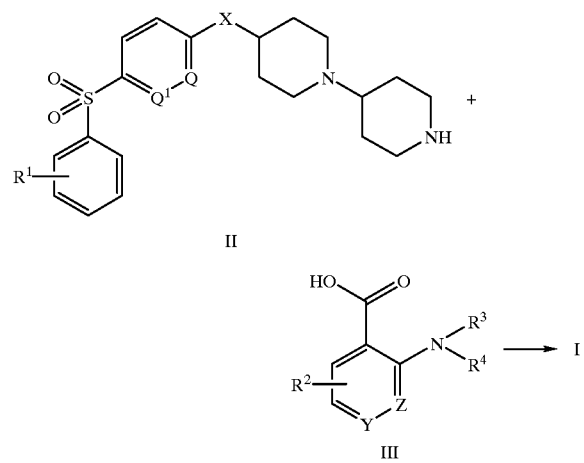

The reaction is carried out using methods well known in the art, such as by treatment of the amine II with the acid III and a dehydrating agent such as EDCI and HOBt in the presence of a base such as N-methyl-morpholine, in a solvent such as $CH_2Cl_2$ or DMF.

Starting materials of formula II are made by various processes known in the art. In the following reaction schemes, typical procedures and reagents are shown for preparing the starting materials, although those skilled in the art will recognize that preparation of the compounds of the invention is not limited to these procedures or reagents.

Compounds of formula IIa wherein Q and $Q^1$ are each —CH= and X is —$CH_2$— can be made according to Scheme A:

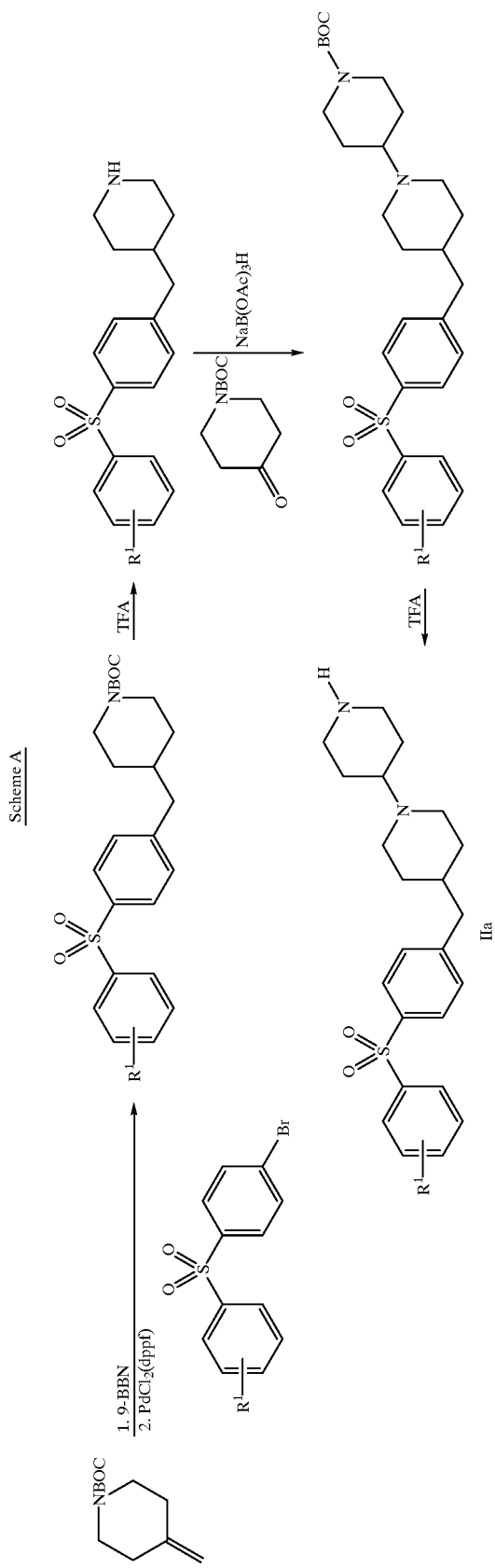

Compounds of formula IIb wherein Q and Q¹ are each —CH=, R¹ is
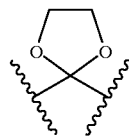
can be made according to Scheme B:
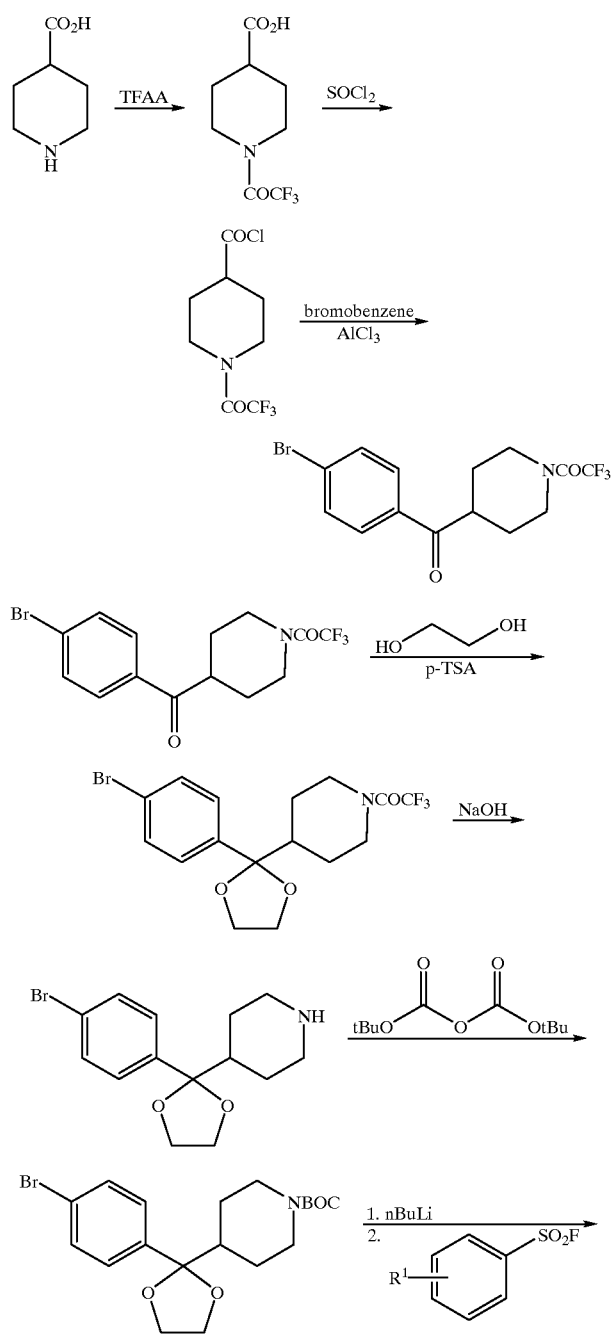

-continued
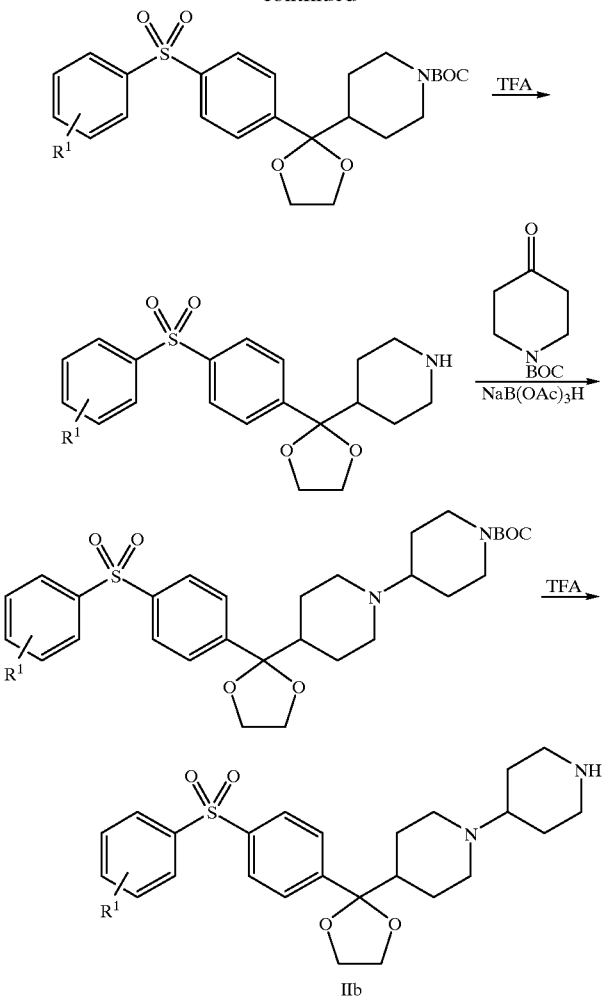
IIb
Compounds of formula IIc wherein Q and Q$^1$ are each —CH=, R$^1$ is
can be made according to Scheme C,
Scheme C
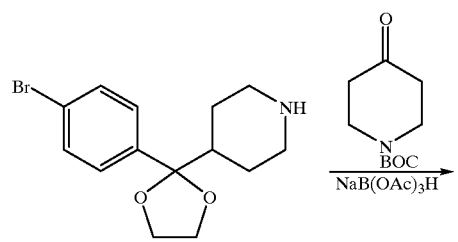

-continued

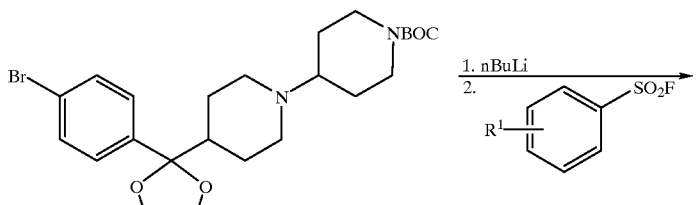

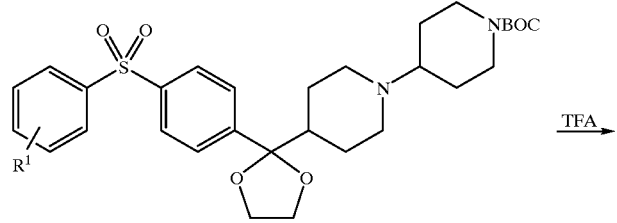

IIc

This process comprises essentially the same procedures as in Scheme B, but reverses the order of attaching the phenylsulfonyl fluoride and the piperidone.

Starting materials of formula IId wherein X is —CH$_2$—, Q is —CH= and Q$_1$ is —N= can be made according to Scheme D:

Scheme D

-continued

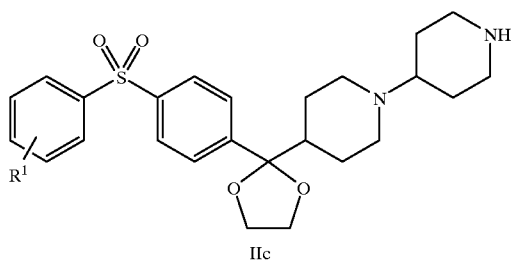

IId

Starting materials of formula IIe wherein X is —CH$_2$—, Q is —N= and Q$_1$ is —CH= can be made according to Scheme E:

Scheme E

Alternatively, compounds of formula IIa wherein Q and Q$^1$ are each —CH= and X is —CH$_2$— can be made according to Scheme F:

Scheme F

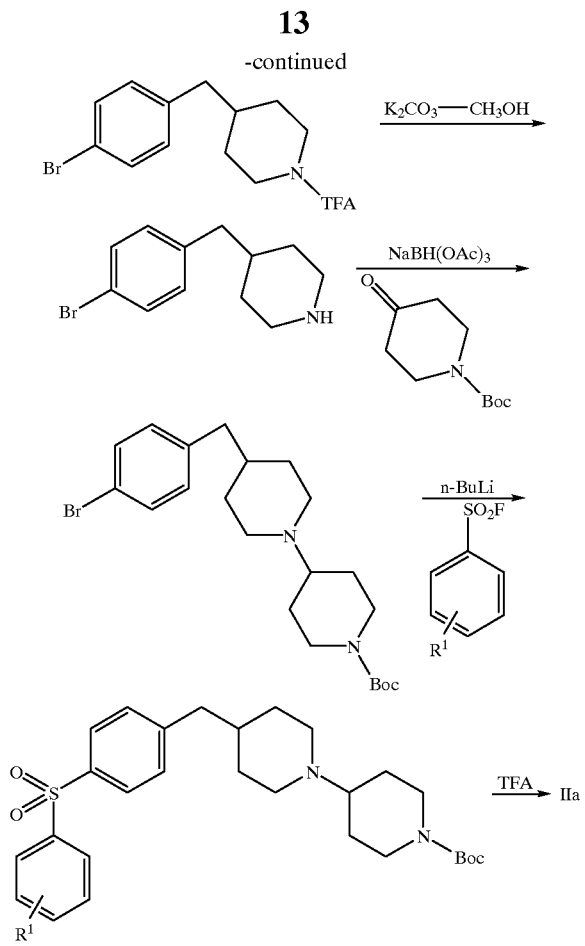

In the above processes it is sometimes desirable and/or necessary to protect certain groups during the reactions. Conventional protecting groups, familiar to those skilled in the art, are operable. After the reaction or reactions, the protecting groups may be removed by standard procedures.

The above reactions may be followed if necessary or desired by one or more of the following steps; (a) removing any protective groups from the compound so produced; (b) converting the compound so-produced to a pharmaceutically acceptable salt, ester and/or solvate; (c) converting a compound in accordance with formula I so produced to another compound in accordance with formula I, and (d) isolating a compound of formula I, including separating stereoisomers of formula I.

Based on the foregoing reaction sequence, those skilled in the art will be able to select starting materials needed to produce any compound in accordance with formula I.

The compounds of formula I exhibit selective m2 and/or m4 muscarinic antagonizing activity, which has been correlated with pharmaceutical activity for treating cognitive disorders and/or symptoms thereof. Examples of cognitive disorders are Alzheimers disease and senile dementia, with treatment resulting in improvement in memory and learning.

The compounds of formula I display pharmacological activity in test procedures designated to indicate m1 and m2 muscarinic antagonist activity. The compounds are non-toxic at pharmaceutically therapeutic doses. Following are descriptions of the test procedures.

Muscarinic Binding Activity

The compound of interest is tested for its ability to inhibit binding to the cloned human m1, m2, m3, and m4 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homogenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 pg of protein assay for the m1, m2, and m4 containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 μM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for $IC_{50}$ values (i.e. the concentration of compound required to inhibit binding by 50%) using the EBDA computer program (McPherson, 1985). Affinity values (Ki) were then determined using the following formula (Cheng and Prusoff, 1973);

$$K_i = \frac{IC_{50}}{1 + \left[\frac{\text{concentration of radioligand}}{\text{affinity } (K_D) \text{ of radioligand}}\right]}$$

Hence, a lower value of $K_i$ indicates greater binding affinity.

To determine the degree of selectivity of a compound for binding the m2 receptor, the $K_i$ value for m1 receptors was divided by the $K_i$ value for m2 receptors. A higher ratio indicates a greater selectivity for binding the m2 muscarinic receptor.

Microdialysis Methodology

The following procedure is used to show that a compound functions as an m2 antagonist.

Surgery: For these studies, male Sprague-Dawley Rats (250–350 g) were anesthetized with sodium pentobarbital (54 mg/kg, ip) and placed on a Kopf sterotaxic apparatus. The skull was exposed and drilled through to the dura at a point 0.2 mm anterior and 3.0 mm lateral to the bregma. At these coordinates, a guide cannula was positioned at the outer edge of the dura through the drilled opening, lowered perpendicularly to a depth of 2.5 mm, and permanently secured with dental cement to bone screws. Following the surgery, rats were given ampicillin (40 mg/kg, ip) and individually housed in modified cages. A recovery period of approximately 3 to 7 days was allowed before the microdialysis procedure was undertaken.

Microdialysis: All of the equipment and instrumentation used to conduct in vivo microdialysis was obtained from Bioanalytical Systems, Inc. (BAS). The microdialysis procedure involved the insertion through the guide cannula of a thin, needle-like perfusable probe (CMA/12, 3 mm×0.5 mm) to a depth of 3 mm in striatum beyond the end of the guide. The probe was connected beforehand with tubing to a microinjection pump (CMA/100). Rats were collared, tethered, and, following probe insertion, were placed in a large, clear, plexiglass bowl with litter material and access to food and water. The probe was perfused at 2, μl/min with Ringer's buffer (NaCl 147 mM; KCl 3.0 mM; $CaCl_2$ 1.2 mM; $MgCl_2$ 1.0 mM) containing 5.5 mM glucose, 0.2 mM L-ascorbate, and 1 μM neostigmine bromide at pH 7.4). To achieve stable baseline readings, microdialysis was allowed to proceed for 90 minutes prior to the collection of fractions. Fractions (20 μl) were obtained at 10 minute intervals over a 3 hour period using a refrigerated collector (CMA/1 70 or 200). Four to five baseline fractions were collected, following which the drug or combination of drugs to be tested was administered to the animal. Upon completion of the collection, each rat was autopsied to determine accuracy of probe placement.

Acetylcholine (ACh) analysis: The concentration of ACh in collected samples of microdialysate was determined using HPLC/electrochemical detection. Samples were auto-injected (Waters 712 Refrigerated Sample Processor) onto a polymeric analytical HPLC column (BAS, MF-6150) and eluted with 50 mM $Na_2HPO_4$, pH 8.5. To prevent bacterial growth, Kathon CG reagent (0.005%) (BAS) was included in the mobile phase. Eluent from the analytical column, containing separated ACh and choline, was then immediately passed through an immobilized enzyme reactor cartridge (BAS, MF-6151) coupled to the column outlet. The reactor contained both acetylcholinesterase and choline oxidase covalently bound to a polymeric backbone. The action of these enzymes on ACh and choline resulted in stoichiometric yields of hydrogen peroxide, which was electrochemically detected using a Waters 460 detector equipped with a platinum electrode at a working potential of 500 mvolts. Data acquisition was carried out using an IBM Model 70 computer equipped with a microchannel IEEE board. Integration and quantification of peaks were accomplished using "Maxima" chromatography software (Waters Corporation). Total run time per sample was 11 minutes at a flow rate of 1 ml/min. Retention times for acetylcholine and choline were 6.5 and 7.8 minutes, respectively. To monitor and correct for possible changes in detector sensitivity during chromatography, ACh standards were included at the beginning, middle and end of each sample queue.

Increases in ACh levels are consistent with presynaptic m2 receptor antagonism.

Data for representative and/or preferred compounds of the present invention are as follows (compounds were administered at a dose of 10 mg/kg PO):

RESULTS OF THE TESTS

| Ex. | m1 Ki (nM) | m2 Ki (nM) | m3 Ki (nM) | m4 Ki (nM) | m5 Ki (nM) | Microdialysis Maximum % of baseline |
|---|---|---|---|---|---|---|
| 2 | 242.15 | 0.389 | 97.22 | 13.52 | 22.37 | 194 |
| 7 | 650.4 | 0.886 | 697.57 | 61.36 | 84.51 | 180 |
| 3E | 42.83 | 0.115 | 16.05 | 5.36 | 4.00 | 188 |
| 2F | 145.00 | 0.513 | 56.5 | 9.75 | 16.80 | 186 |
| 7A | 658.25 | 0.225 | 612.50 | 33.25 | 41.80 | 150 |

For the compounds of this invention, the following ranges of muscarinic antagonistic activity were observed:

m1: 42.8 nM to 2071.3 nM m2: 0.12 nM to 9.65 nM m3: 7.3 nM to 3127.5 nM m4: 5.4 nM to 968.9 nM m5; 2.7 nM to 928.0 nM

The selectivity ranges are as follows:

m1/m2: 52 to 2925 m3/m2: 6 to 148 m4/m2: 4 to 162 m5/m2: 4 to 402

The microdialysis range is 112 to 194%.

In the aspect of the invention relating to a combination of a compound of formula I with an acetylcholinesterase inhibitor, examples of acetylcholinesterase inhibitors are E-2020 (available from Eisai Pharmaceutical) and heptylphysostigmine.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

When a compound of formula I is used in combination with an acetylcholinesterase inhibitor to treat cognitive disorders these two active components may be co-administered simultaneously or sequentially, or a single pharmaceutical composition comprising a compound of formula I and an acetylcholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the acetylcholin-esterase inhibitor may range from 0.001 to 100 mg/kg body weight.

The invention disclosed herein is exemplified by the following preparation and examples which should not be construed to limit the scope of the disclosure. Alternative mechanistic pathways and analogous structures may be apparent to those skilled in the art. In the examples, the following terms are abbreviated: room temperature (RT); trifluoro-acetic acid (TFA); trifluoroacetic anhydride (TFM); dimethyl-formamide (DMF); 9-borabicyclo[3.3.1]nonane (9-BBN); ethyl acetate (EtOAc); tetrahydrofuran (THF); ethyl (Et); acetyl (Ac); propyl (Pr); t-butoxycarbonyl (BOC); 1-hydroxybenzotriazole (HOBt); 1-(3-dimethyl aminopropyl)-3-ethylcarbodiimide hydrochloride (EDCI); p-toluene sulfonic acid (p-TSA); dimethylsulfoxide (DMSO); 3-chloroperoxy benzoic acid (mCPBA); 2-diethylaminoethyl chloride hydrochloride (DEC); dibromodimethylhydantion (DBDMH).

EXAMPLE 1

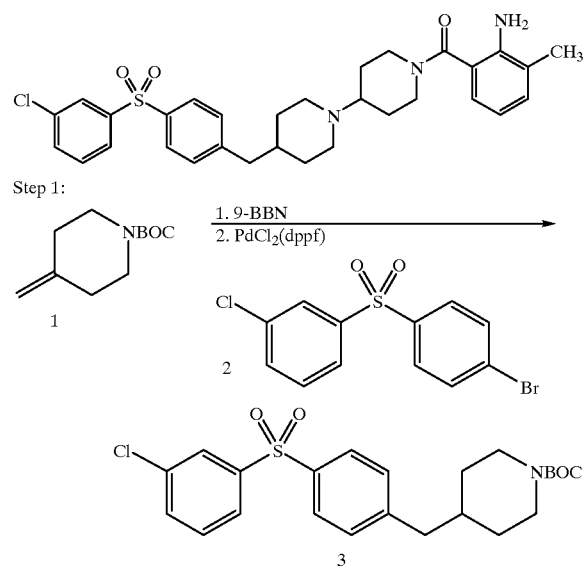

To 1 (3.23 g; 16.38 mmol) was added, at RT, 9-BBN (34.40 ml of a 0.5M solution in THF). The resulting solution was heated at reflux for 30 min., cooled to RT and added to a mixture containing 2 (4.93 g; 14.89 mmol), $K_2CO_3$ (2.05 g), $PdCl_2(dppf)$ (608 mg; 5 mol %), $Ph_3As$ (379 mg), DMF (25 ml) and $H_2O$ (2.68 ml). The resulting mixture was heated at 50° C. for 1 h, cooled and poured into ice water. After extraction with EtOAc (3×25 ml), the combined organic layers were washed with brine, dried over $MgSO_4$, filtered and evaporated to give a dark oil which was purified by column chromatography (silica gel; 4:1 hexanes:EtOAc), to give, after evaporation of the appropriate fractions, 5.24 9 of intermediate 3 (79% yield), which was used directly in the next step.

Step 2:

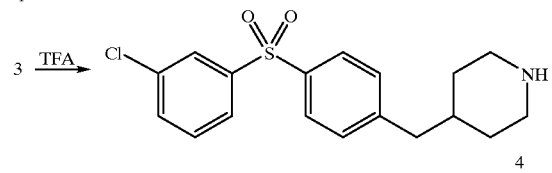

To a cooled (0° C.) mixture of 3 (4.74 g; 10.5 mmol), $CH_2Cl_2$ (35 ml) and $H_2O$ (0.19 ml) was added, dropwise, TFA (7 ml). The cooling bath was removed and the mixture was stirred for 30 min. TFA (1.0 ml) and $H_2O$ (0.18 ml) were added. The stirring was continued for 2 h, the volatile materials were removed in vacuo, $CH_2Cl_2$ (20 ml) and 10% NaOH (2 ml) were added, and the resulting mixture was stirred for 3 min. The $CH_2Cl_2$ layer was removed, the aqueous layer was extracted with $CH_2Cl_2$ (3×5 ml), the organic extracts were dried over $Na_2SO_4$, filtered and evaporated to give 4 as a white foam (3.10 g) in 88% yield. mp (TFA salt): decomposition above 196° C.

Step 3:

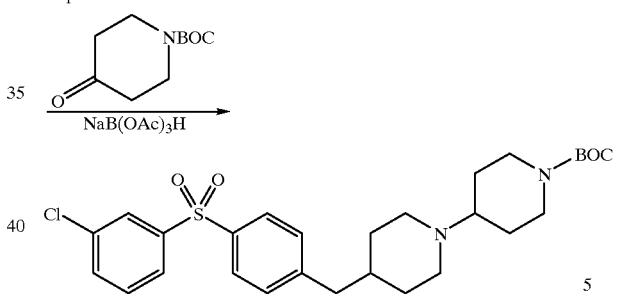

To a solution of 4(1.69 9), N-tert-butoxy piperidone (4.80 g), $CH_2Cl_2$ (12 ml) and HOAc (0.28 ml) was added NaB(OAc)$_3$H (1.42 g) in four portions over 15 min. The resulting solution was stirred for 4 h when HOAc (0.14 ml) and NaB(OAc)$_3$H (1.42 g) were added. After stirring at RT for 16 h, the reaction was diluted with $CH_2Cl_2$ (50 ml) and made basic with 2N NaOH (15 ml). The $CH_2Cl_2$ layer was removed and the aqueous layer was extracted with $CH_2Cl_2$ (2×15 ml). The organic extracts were combined, washed with water and brine, dried over $MgSO_4$, then filtered and evaporated to give a crude solid which was purified by silica gel chromatography (320 g silica; 1:1 hexanes:EtOAc, then 76:19:5 EtOAc:hexanes:Et$_3$N as eluant) to give the product, 5, as a waxy solid (2.27 g) in 88% yield.

Step 4

Intermediate 5 was subjected to the same reaction conditions as in Step 2, using $CH_2Cl_2$ (10 ml), TFA (2 ml), $H_2O$ (0.046 ml) and 5 (1.37 g). After work up, the free amine was isolated as a clear oil (0.33 g) in 46% yield.

Step 5

To a mixture of the product of Step 4 (61 mg), DMF (2.0 ml), HOBt (28 mg), iPr$_2$EtN (0.10 ml) and 2-amino-3-methyl benzoic acid (32 mg) was added EDCI (41 mg). The resulting solution was stirred at RT for 16 h, diluted with EtOAc (10 ml) and 2N NaOH (1 ml). The aqueous layer was extracted with EtOAc (3×4 ml) and the combined organic extracts were dried over Na$_2$SO$_4$, filtered and evaporated to give a dark oil which was purified by preparative plate chromatography (1000 μM; silica adsorbent; 95:5 EtOAc:Et$_3$N eluant), to give, after isolation of the appropriate band, the title compound as a white foam (57 mg) in 84% yield.

Step 6

The product of Step 5 (57 mg) was dissolved in EtOAc (2.0 ml), cooled to 0° C. and HCl (50 μL of a 4.0M solution in 1,4-dioxane) was added. The resulting mixture was warmed to RT, diluted with Et$_2$O, centrifuged, washed with Et$_2$O (2×2 ml) and dried under vacuum to give the hydrochloride of the title compound as a white solid (51 mg).

Using a similar procedure, substituting the appropriate diaryl sulfone in step 1 and the appropriate carboxylic acid in step 5, compounds of the following formula were prepared

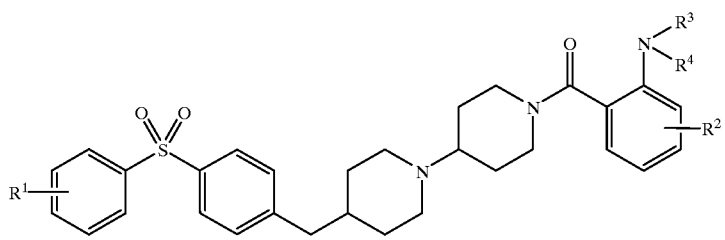

wherein the variables are as defined in the table:

| Ex. | R$^1$ group | NR$^3$R$^4$/R$^2$ group | Physical data |
|---|---|---|---|
| 1A | 4-H$_3$CO-phenyl | 2-NHCH$_2$CH$_3$-phenyl | HRMS found 576.2892 |
| 1B | 4-H$_3$CO-phenyl | 2-NH$_2$-phenyl | mp: decomp. >147° C. |
| 1C | 4-H$_3$CO-phenyl | 2-NH$_2$-3-CH$_3$-phenyl | mp: decomp. >156° C. |
| 1D | 4-H$_3$CO-phenyl | 2-NH$_2$-3-OCH$_3$-phenyl | mp: decomp. >146° C. |
| 1E | 4-H$_3$CO-phenyl | 2-NH$_2$-3-Cl-phenyl | mp: decomp. >131° C. |

-continued
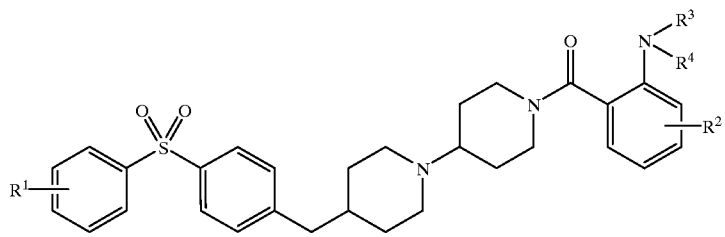
wherein the variables are as defined in the table:
| Ex. | R¹-phenyl group | Aniline group (N-R³R⁴, R²) | Physical data |
|---|---|---|---|
| 1F | 4-H₃CO- | NHCH₃ (R² = H) | mp: decomp. >135° C. |
| 1G | 4-H₃CO- | NH₂, 4-I | mp: decomp. >164° C. |
| 1H | 4-H₃CO- | NH₂, 3,5-diCl | mp: decomp. >145° C. |
| 1I | 3-Cl- | NH₂, 4-F | mp: decomp. >155° C. |
| 1J | 3-Cl- | NH₂, 4-F | mp: decomp. >148° C. |
| 1K | 3-Cl- | NH₂, 3-Cl | mp: decomp. >133° C. |

-continued
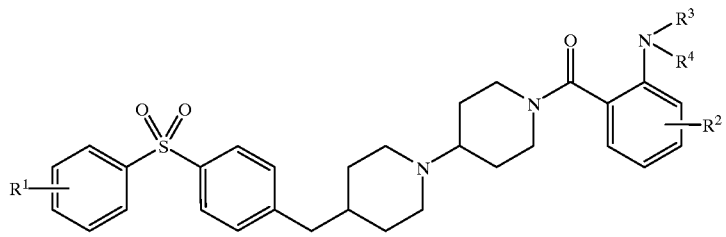
wherein the variables are as defined in the table:
| Ex. | R¹ | NR³R⁴ / R² | Physical data |
|---|---|---|---|
| 1L | 3-Cl-phenyl | 2-(NHCH₂CH₃), 6-Cl | mp: decomp. >69° C. |
| 1M | 3-Cl-phenyl | 2-NH₂-pyridin-3-yl | mp: decomp. >181° C. |
| 1N | 3-Cl-phenyl | 3-NH₂-pyridin-4-yl | mp: decomp. >199° C. |
| 1O | 3-Cl-phenyl | 3-N(CH₃)₂-pyridin-4-yl | mp: decomp. >133° C. |
| 1P | 3-Cl-phenyl | 2-NH₂, 6-Cl | mp: decomp. >165° C. |
| 1Q | 4-OCH₃-phenyl | 2-NH₂, 6-F | mp: decomp. >136° C. |
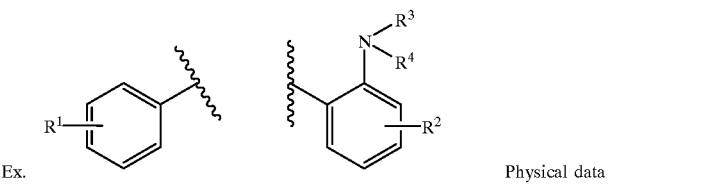
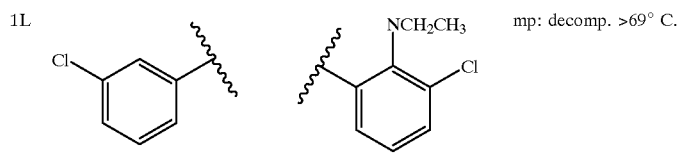
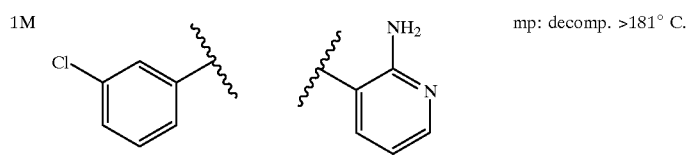
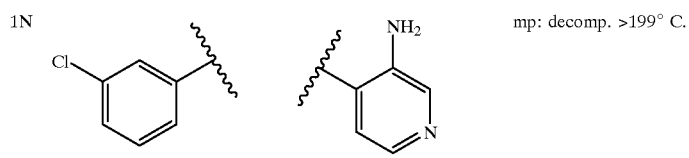
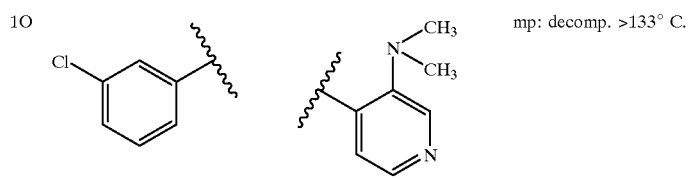
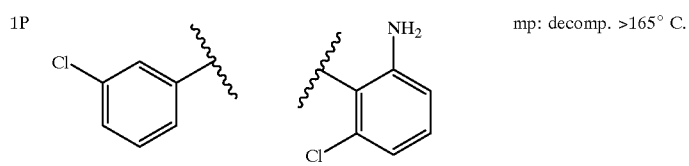
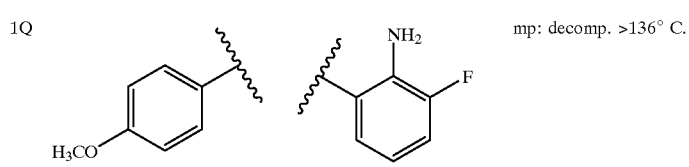

-continued
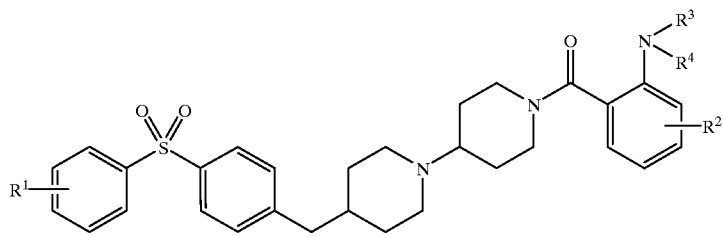
wherein the variables are as defined in the table:
| Ex. | R¹-phenyl group | aniline group | Physical data |
|---|---|---|---|
| 1R | 4-OCH₃ phenyl | 2-NH₂, 3-F phenyl | mp: decomp. >160° C. |
| 1S | 3-Cl phenyl | 2-NH₂, 3-F phenyl | mp: decomp. >138° C. |
| 1T | 3-Cl phenyl | 2-NH₂, 4-I phenyl | mp: decomp. >164° C. |
EXAMPLE 2
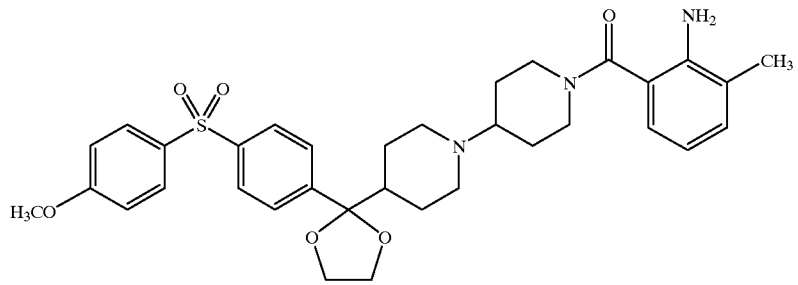

Steps 1–3:

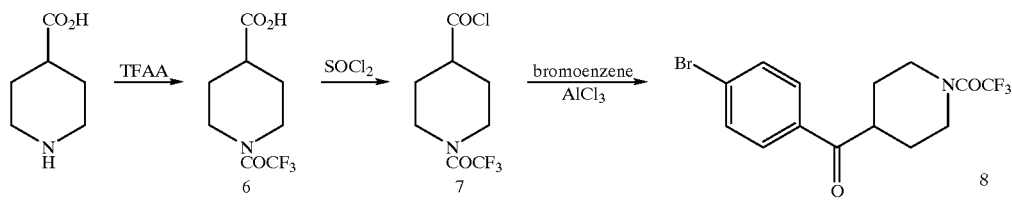

Step 1
Isonipecotic acid (100 g) was cooled to 0C and TFAA (275 ml) was added over 30 min. The resulting mixture was heated at reflux for 3.5 h and then the volatile materials were removed in vacuo. The remaining residue was dissolved in EtOAc (800 ml) and washed with water (2×600 ml). The EtOAc layer was dried over $MgSO_4$, filtered and evaporated to give 6 (174 g) which was used directly in the next step.

Step 2
A solution of 6 (174 g) and $SOCl_2$ (1 l) was heated at reflux for 18 h, then the volatile material was removed by distillation at house vacuum. Hexane (600 ml) was added and then removed in vacuo to give 7 (189 g) which was used directly in the next step.

Step 3
To a solution of 7 (189 g) and bromobenzene (650 ml) was added $AlCl_3$ (207.9 g) in portions, over 30 min. The mixture exothermed to 60° C. over the course of addition of $AlCl_3$. The resulting mixture was heated at reflux for 4 h, cooled to RT, stirred for 16 h and poured into a mixture of ice (2.4 kg) and aqueous HCl (1 l). After stirring for 20 min, the solution was extracted with EtOAc (4 l then 2×2 l), the extracts were combined and washed with water (2 l) and brine (2 l). The extracts were dried with $MgSO_4$, filtered and evaporated to give a dark oil (306.1 g ) which was dissolved in EtOAc (1 l), treated with charcoal, filtered through Celite and evaporated to give 8 (296.6 g) which was used directly in the next step.

Steps 4–5:

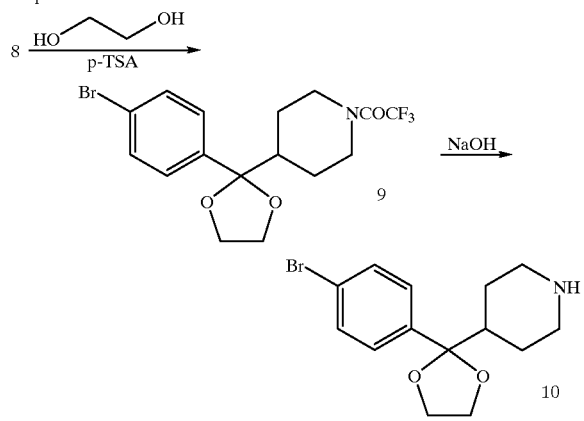

Step 4
A mixture of 8 (296.6 g), toluene (3.0 L) and p-TSA (9.1 g) was heated under reflux, using a Dean-Stark apparatus, until no more water was collected. The reaction mixture was washed with saturated, aqueous $NaHCO_3$ (2 l), brine (1 l), dried over $MgSO_4$, filtered and evaporated to give 300 g of a crude, brown oil which was purified by silica gel chromatography (4400 ml of silica; crude adsorbed onto 600 ml of silica gel; $CH_2Cl_2$ eluant). After evaporation of the appropriate fractions, 9 was isolated as a white solid (105 g) which was used directly in the next step. mp: 68–70° C.

Step 5
9 (39.85 g), EtOH (188 ml) and 2N NaOH (94 ml) were mixed and stirred at RT for 30 min. The volatile materials were removed in vacuo and the resulting thick slurry was diluted with EtOAc (200 ml) and washed with cold water (2×50 ml). The combined aqueous portions were extracted with EtOAc (2×75 ml), the organic extracts were combined, washed with brine (50 ml) and dried over $MgSO_4$. After filtration and evaporation, 10 was isolated as an off-white solid (32.2 g) which was used directly in the next step.

Steps 6–7:

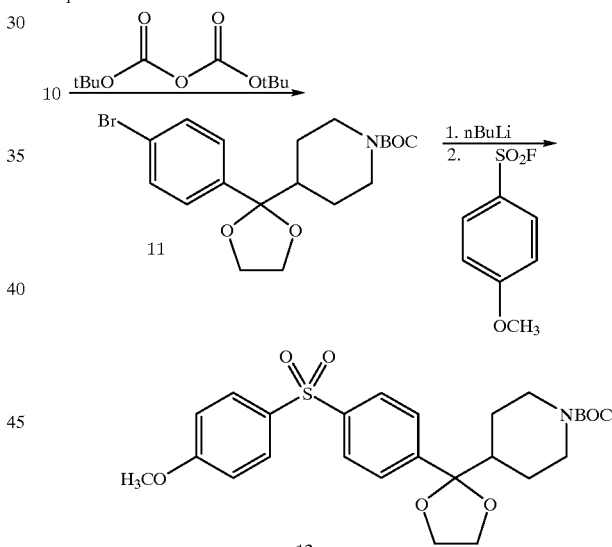

Step 6
To a cooled (0° C.) mixture of $Et_2O$ (295 ml), 10% NaOH (124 ml) and 10 (32.2 g) was added di-tert-butyl dicarbonate (26 g) in portions over a 10 min period. The resulting mixture was stirred for 5 min at 0° C. and 1 h at RT, then diluted with $Et_2O$ (100 ml) and the aqueous layer was removed. The aqueous layer was extracted with $Et_2O$ (2×100 ml) and the $Et_2O$ extracts were combined, washed with water (2×50 ml) and dried over $MgSO_4$. After filtration and evaporation of the solvent, the resulting oil was treated with toluene (100 ml), the toluene was evaporated and the resulting clear oil crystallized on standing to give 11 (34.7 g) which was used directly in the next step. Elemental analysis: $C_{19}H_{26}NO_4Br$:

|       | % C   | % H  | % N  | % Br  |
|-------|-------|------|------|-------|
| calc'd | 55.35 | 6.36 | 3.40 | 19.40 |
| found  | 55.58 | 6.56 | 3.38 | 19.56 |

Step 7

A solution of intermediate 11 (5.00g) and THF (49 ml) was degassed (3×vacuum/Ar purge cycles) and cooled to −72° C. (internal temperature). N-BuLi (5.10 ml of a 2.5M solution in hexanes) was added at such a rate that the internal temperature remained at or below −65° C. and then the mixture was stirred for 7 min. Para-methoxy sulfonyl fluoride (3.00 ml) was added at such a rate that the internal temperature was at or below −60° C. The resulting solution was stirred at low temperature for 10 min; at −40° C for 10 min; 0° C. for 15 min; at 22° C. for 20 min and then it was poured into ice and water. The resulting mixture was extracted with EtOAc (1×150 ml; 3×50 ml), the combined organic extracts were washed with brine, dried over $MgSO_4$, filtered and evaporated to give a crude gold oil (8.35 g) which was purified by silica gel chromatography (210 g silica; 4:1 hexanes:EtOAc then 2:1 hexanes:EtOAc as eluant). After evaporation of the appropriate fractions, 12 (4.35 g) was isolated as a white solid (71% yield). mp: 184–185° C.

Step 8

12 (2.27 g) was treated as in Example 1, Step 2, using $CH_2Cl_2$ (29 ml), TFA (5.82 ml), $H_2O$ (0.099 ml). After work up, the de-protected piperidine derivative was isolated as a yellow solid (2.27 g) and used directly in the next step.

Step 9

The product of Step 8 (2.27 g) was treated as in Example 1, Step 3, using N-tert-butoxy piperidone (5.68 g), $CH_2Cl_2$ (28 ml), HOAc (0.32 ml) and $NaB(OAc)_3H$ (1.68 g). After work up and purification, the product (2.60 g) was isolated as a white foam in 79% yield. HRMS: calc'd: $M.H^+$: $C_{31}H_{43}N_2O_7S$: 587.2791; measured: 587.2805.

Step 10

The product of Step 9 (2.60 g) was treated as in Example 1, Step 2, using $CH_2Cl_2$ (22 ml), TFA (4.43 ml), $H_2O$ (0.08 ml). After work up, the product was isolated as a white solid (1.62 g) in 75% yield. Elemental analysis: $C_{26}H_{34}N_2O_5S.H_2O$:

|       | % C   | % H  | % N  | % S  |
|-------|-------|------|------|------|
| calc'd | 61.88 | 7.19 | 5.55 | 6.35 |
| found  | 61.76 | 6.85 | 5.16 | 6.44 |

Step 11

The product of Step 10 (1.20 g) was treated as in Example 1, Step 5, using DMF (6.5 ml), HOBt (500 mg), $iPr_2EtN$ (1.72 ml), 2-amino-3-methyl benzoic acid (560 mg) and EDCI (710 mg). After work up and purification, the title compound (1.39 g) was isolated in its free base form as a white foam in 91% yield.

Step 12

The product of Step 11 (1.39 g) was treated as in Example 1, Step 6, using EtOAc (23 ml), $CH_2Cl_2$ (1.8 ml) and HCl (1.25 ml of a 4.0M solution in 1,4-dioxane). After work up, the resulting white solid was purified by recrystallization from isopropanol. Filtration of the resulting solid and drying under vacuum (1 mm Hg) at 75° C. for 18 h gave the hydrochloride of the title compound (1.10 g) as a white solid in 77% yield. mp: 167.5–169° C.

Using a similar procedure, substituting the appropriate sulfonyl fluoride in step 6 and the appropriate carboxylic acid in step 11, compounds of the following formula were prepared

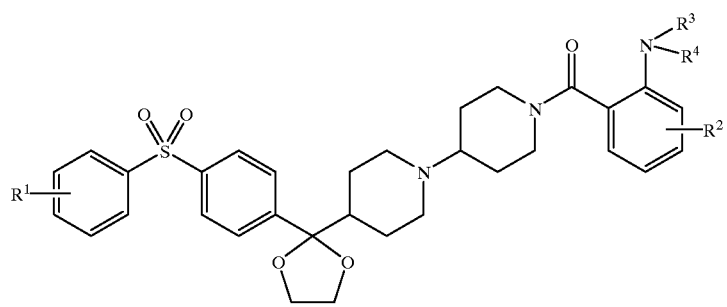

wherein the variables are as defined in the table:

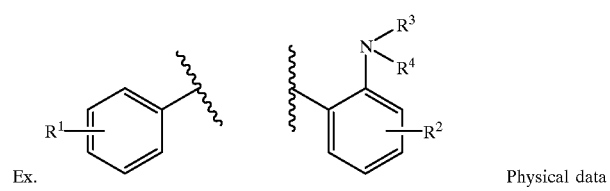

Ex.    Physical data

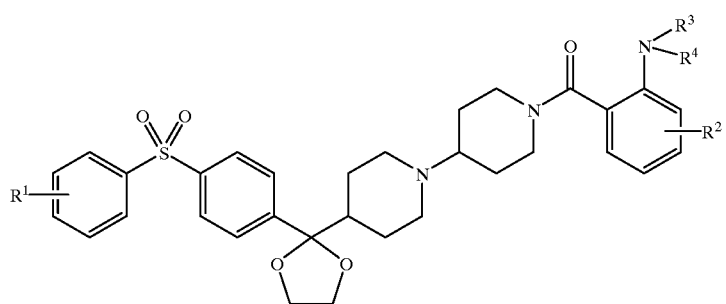
wherein the variables are as defined in the table:
| Ex. | R¹ (phenyl) | NR³R⁴ / R² (phenyl) | Physical data |
|---|---|---|---|
| 2A | 3-Cl, 4-OCH₃ | 2-NH₂, 3-CH₃ | HRMS found 654.2391 |
| 2B | 3-Cl, 4-OCH₃ | 2-NH₂, 6-CH₃ | HRMS found 654.2391 |
| 2C | 3-Cl, 4-OCH₃ | 2-NH₂ | mp: decomp. >170° C. |
| 2D | 4-OCH₃ | 2-NH₂, 3-Cl | mp: decomp. >161° C. |
| 2E | 4-OCH₃ | 2-NH₂, 3-F, 5-F | mp: decomp. >145° C. |
| 2F | 4-OCH₃ | 2-NH₂, 3-F | mp: decomp. >139° C. |

-continued
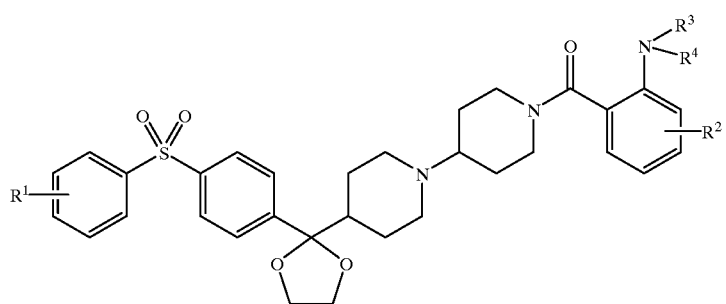
wherein the variables are as defined in the table:
| Ex. | R¹ group | NR³R⁴/R² group | Physical data |
|---|---|---|---|
| 2G | 4-H₃CO-C₆H₄- | 2-NH₂, 4-F phenyl | mp: decomp. >150° C. |
| 2H | 4-H₃CO-C₆H₄- | 2-NH₂, 5-F phenyl | mp: decomp. >147° C. |
| 2I | 4-H₃CO-C₆H₄- | 2-NH₂, 3-OCH₃ phenyl | mp: decomp. >145° C. |
| 2J | 4-H₃CO-C₆H₄- | 3-amino-pyridin-4-yl | mp: decomp. >185° C. |
| 2K | 4-H₃CO-C₆H₄- | 2-amino-pyridin-3-yl | mp: decomp. >238° C. |
wherein the variables are as defined in the table:

EXAMPLE 3

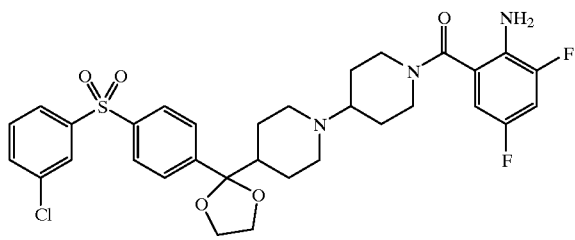

Step 1:

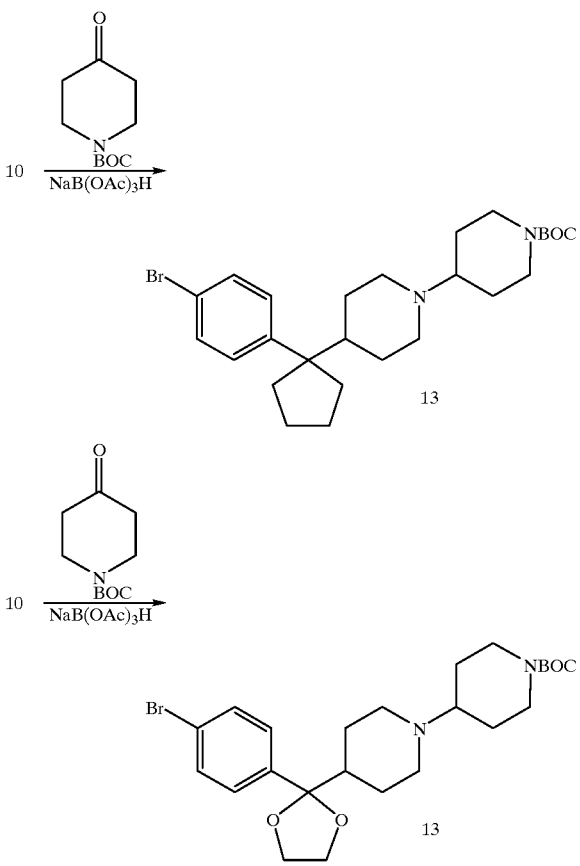

Step 1

10 (25.03 g) was treated as in Example 1, Step 3, using N-tert-butoxy piperidone (59 g), CH$_2$Cl$_2$ (185 ml), HOAc (4.22 ml) and NaB(OAc)$_3$H (22 g). After work up and purification, 13 (31.0g) was isolated as a white powder in 85% yield and was used directly in the next step.

Step 2

To a cooled (−75° C. (internal temperature)) solution of 13 (3.49 g) and THF (28 ml) was added n-BuLi (2.96 ml of a 2.5M solution in hexanes) at such a rate that the internal temperature remained at −75° C. and then stirred for 20 min. Meta-chloro benzene sulfonyl fluoride (1.10 ml) was added at such a rate that the internal temperature was at or below −72° C. The resulting solution was slowly warmed to RT, stirred at RT for 16 h and poured into ice and water. The resulting mixture was extracted with EtOAc (50 ml), the pH of the aqueous layer was adjusted to 11 with solid NaOH (4 g) and the resulting aqueous layer was extracted with EtOAc (3×25 ml). The combined organic extracts were washed with brine, dried over MgSO$_4$, filtered and evaporated to give a crude oil which was purified by silica gel chromatography (179 g silica; 76:19:5 hexanes:EtOAc:Et$_3$N; 47.5:47.5:5 hexanes:EtOAc:Et$_3$N; 76:19:5 EtOAc:hexanes:Et$_3$N as eluant). After evaporation of the appropriate fractions, the product (1.78 g) was isolated as a white solid in 43% yield and used directly in the next step.

Step 3

The product of Step 2 (0.32 g) was treated as in Example 1, Step 2,, using CH$_2$Cl$_2$ (3 ml), TFA (0.6 ml), H$_2$O (9.6 EL). After work up, the product was isolated as a clear oil (193.5 mg) in 73% yield and used directly in the next step.

Steps 4–5:

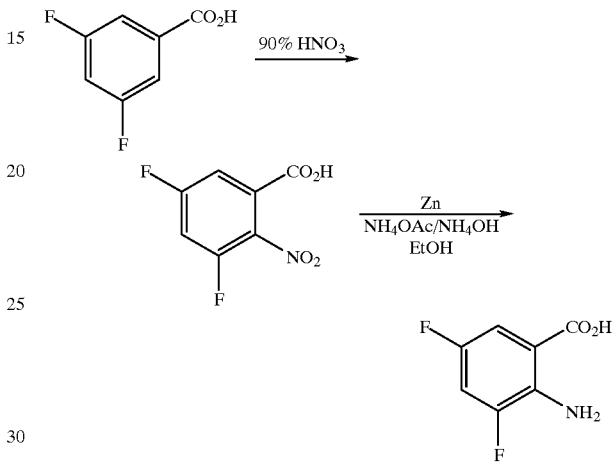

Step 4

To 3,5difluorobenzoic acid (1.0 g) was added HNO$_3$ (90% fuming; 3 ml). The homogeneous solution was stirred at RT for 20 h, then poured into ice water (150 ml). The solution was extracted with CH$_2$Cl$_2$, and the combined CH$_2$Cl$_2$ layers were dried over Na$_2$SO$_4$. Filtration and concentration gave the desired intermediate (435 mg) as a white solid in 34% yield and was used directly in the next step.

Step 5

The product of Step 4 (435 mg), NH$_4$OAc (100 mg) and conc. NH$_4$OH (10 ml) were mixed together and Zn (1.0 g) was added in portions. (Caution: exotherm was detected after addition of Zn to the mixture!) After several minutes, the resulting mixture was heated at reflux for 1 h. The solution was cooled, filtered and concentrated to provide a beige solid. The solid was triturated with hot water, collected and dried by co-evaporation with toluene (3×10 ml) to give the desired product (200 mg) as a white solid in 54% yield which was used directly in the next step.

Step 6

The product of Step 3 (100 mg) was treated as in Example 1, Step 5, using DMF (0.75 ml), HOBt (41 mg), iPr$_2$EtN (0.14 ml) and the product of Step 5 (55.5 mg) and DEC (58 mg). After work up and purification, the title compound (96 mg) was isolated as a free base, a white foam, in 74% yield.

Step 7

The product of Step 6 (96 mg) was treated as in Example 1, Step 6, using EtOAc (1.5 ml) and HCl (56 μL of a 4.0M solution in 1,4-dioxane). After work up, the title compound was isolated as its hydrochloride salt (80.4 mg) as a white solid in 79% yield. mp: with decomposition >155° C.

Using a similar procedure, prepare compounds of the formula:

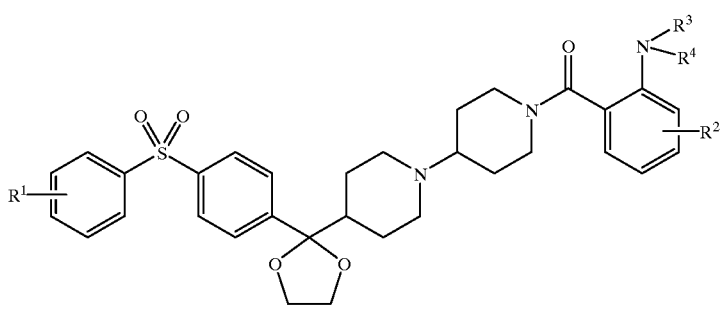
wherein the variables are as defined in the table:
| Ex. | 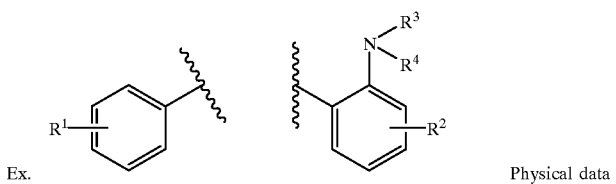 R¹ | R³−N−R⁴, R² | Physical data |
|---|---|---|---|
| 3A | 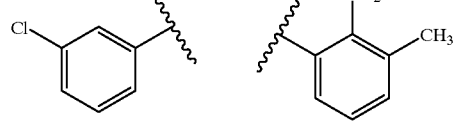 Cl (meta) | NH₂, CH₃ | mp: decomp. >92° C. |
| 3B | Cl (meta) | NH₂ | mp: decomp. >174° C. |
| 3C | Cl (meta) | NH₂, F | mp: decomp. >124° C. |
| 3D | Cl (meta) | NH₂, OCH₃ | mp: decomp. >159° C. |
| 3E | Cl (meta) | NH₂, F | mp: decomp. >154° C. |
| 3F | Cl (meta) | NH₂, F | mp: decomp. >165° C. |

-continued

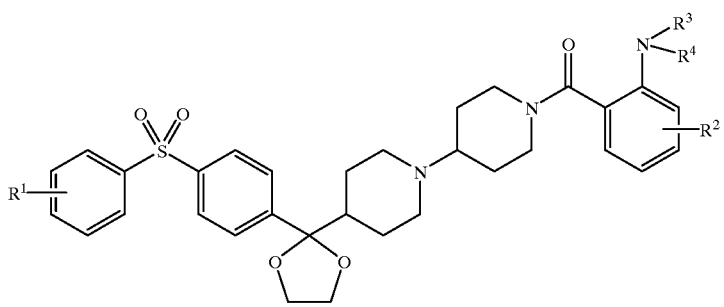

wherein the variables are as defined in the table:

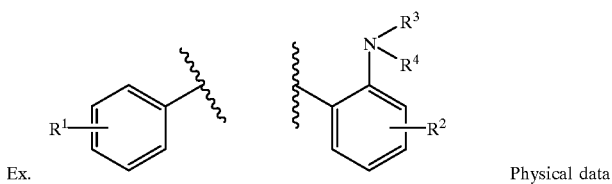

| Ex. | R¹ group | R²/R³/R⁴ group | Physical data |
|---|---|---|---|
| 3G | 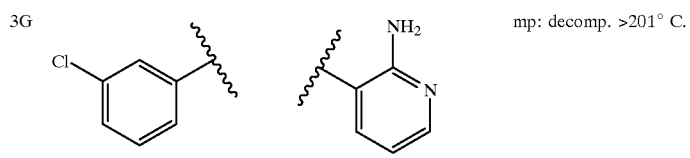 | | mp: decomp. >201° C. |
| 3H | 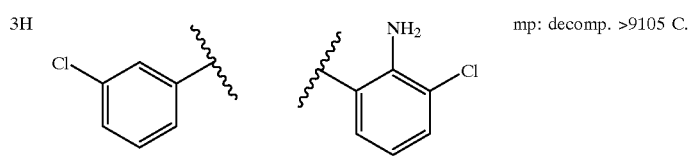 | | mp: decomp. >9105 C. |
| 3I | 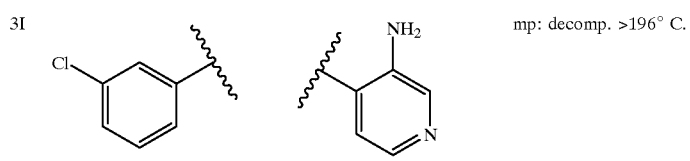 | | mp: decomp. >196° C. |

EXAMPLE 4

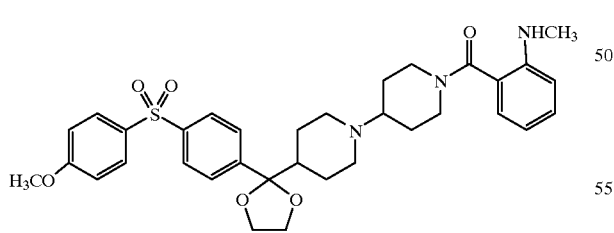

The product of Example 2, Step 10 (44 mg), CH₃CN (0.5 ml), THF (0.25 ml), iPr₂EtN (0.10 ml) and N-methyl isatoic anhydride (33 mg) were mixed together and stirred for 24 h at RT. After removing all volatile materials, the resulting residue was purified by preparative plate chromatography (500 ;μM; silica adsorbent; 95:5 EtOAc:Et₃N eluant) to give the title compound as its free base form (42.1 mg) in 75% yield.

The free base form of the title compound was treated as in Example 1, Step 6, to give the hydrochloride form: mp: decomposition above 168° C.

EXAMPLE 5

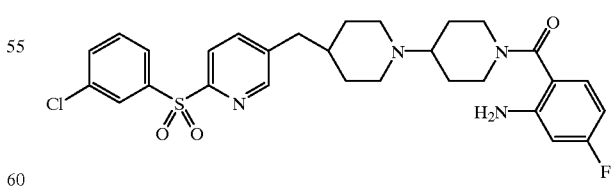

Steps 1–2:

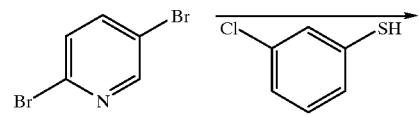

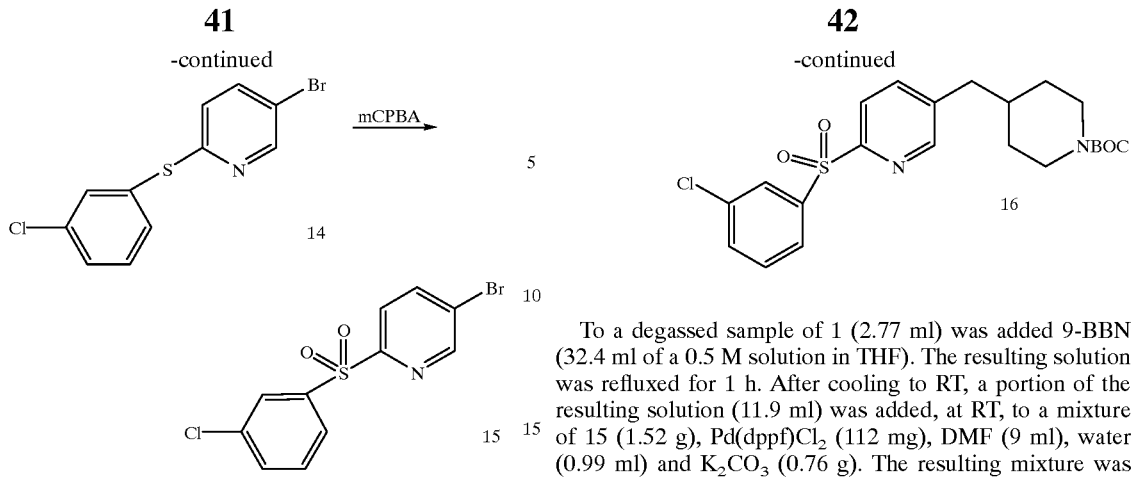

Step 1

NaH (2.32 g of a 60% dispersion in mineral oil) was washed with hexane (3 ml) and then DMSO (21 ml) was added. The resulting mixture was cooled to 0aC and 3-chloro thiophenol (4.90 ml) was added dropwise and the resulting mixture was stirred for 5 min at 0° C. and 1 h at RT. 2,5-Dibromopyridine (10.0 g) was added all at once and the resulting mixture was heated at 80° C. for 1 h. The reaction mixture was diluted with EtOAc (200 ml) and washed with cold water. The aqueous layer was extracted with EtOAc (2×50 ml) and the combined EtOAc extracts were washed with brine, dried over MgSO$_4$, filtered and evaporated to give a solid residue which was purified by column chromatography (silica adsorbent; 30:1 hexanes:EtOAc eluant). After evaporation of the appropriate fractions, 14 was isolated as a solid (3.74 g) in 30% yield and was used directly in the next step.

Step 2

To a cooled (0° C.) solution of 14 (2.95 g) and CH$_2$Cl$_2$ (49 ml) was added mCPBA (4.35 g) in portions over 3 min. The resulting mixture was stirred for 5 min at 0° C., then at RT for 18 h, at which time mCPBA (2.18 g) and CH$_2$Cl$_2$ (5 ml) were added. After stirring for 18 h at RT, 10% Na$_2$S$_2$O$_3$ was added and the CH$_2$Cl$_2$ layer was removed. The aqueous layer was extracted with CH$_2$Cl$_2$, the CH$_2$Cl$_2$ extracts were combined, washed with brine, dried over MgSO$_4$, filtered and washed with 10% NaOH. The CH$_2$Cl$_2$ extracts were dried over MgSO$_4$, filtered and evaporated to give a solid residue which was further purified by column chromatography (silica adsorbent; 8:1 hexanes:EtOAc, then 4:1 hexanes:EtOAc eluant). After evaporation of the appropriate fractions, 15 was isolated as a white solid (1.52 g) in 47% yield and was used directly in the next step.

Step 3:

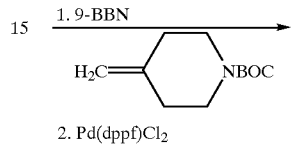

To a degassed sample of 1 (2.77 ml) was added 9-BBN (32.4 ml of a 0.5 M solution in THF). The resulting solution was refluxed for 1 h. After cooling to RT, a portion of the resulting solution (11.9 ml) was added, at RT, to a mixture of 15 (1.52 g), Pd(dppf)Cl$_2$ (112 mg), DMF (9 ml), water (0.99 ml) and K$_2$CO$_3$ (0.76 g). The resulting mixture was heated at 60° C. for 2.5 h. After cooling to RT and pouring into water, the pH was adjusted to 11 with 10% NaOH and the mixture was extracted with EtOAc (3×25 ml). The combined organic extracts were dried with brine and MgSO$_4$, filtered and evaporated. The resultant crude product was further purified by column chromatography (177 g silica adsorbent; 1:2 EtOAc:hexanes eluant) to give 16 as a white foam (1.57 g) in 76% yield.

Step 4

16 (1.52 g) was treated as in Example 1, Step 2, using CH$_2$Cl$_2$ (17 ml), TFA (3.4 ml), H$_2$O (0.060 ml). After work up, the desired amine was isolated as an oil (1.17 g) in 99% yield.

Step 5

The product of Step 4 (1.09 g) was treated as in Example 1, Step 3, using N-tert-butoxy piperidone (2.47 g), CH$_2$Cl$_2$ (10 ml), HOAc (0.18 ml) and NaB(OAc)$_3$H (0.92 g). After work up and purification, the product (1.17 g) was isolated as a white foam in 71% yield. HRMS: calc'd: M.H$^+$: C$_{27}$H$_{37}$N$_3$O$_4$SCl: 536.2164; measured: 536.2153.

Step 6

The product of Step 5 (1.06 g) was treated as in Example 1, Step 2, using CH$_2$Cl$_2$ (10 ml), TFA (2 ml) and H$_2$O (0.036 ml). After work up, the product was isolated as an oil (1.24 g) which was used directly in Step 7.

Step 7

The product of Step 6 (0.10 g) was treated as in Example 1, Step 5, using DMF (0.75 ml), HOBt (41 mg), iPr$_2$EtN (0.14 ml), 2-amino4-fluoro benzoic acid (50 mg) and DEC (58 mg). After work up and purification, the title compound (83 mg) was isolated in its free base form as a foam in 91% yield (over two steps).

Step 8

The free base of Step 7 (83 mg) was treated as in Example 1, Step 6, using CH$_2$Cl$_2$ (1.0 ml) and HCl (0.12 ml of a 4.0M solution in 1,4-dioxane). After work up and purification, the hydrochloride of the title compound (57 mg) was isolated as a white solid in 67% yield. mp: decomposition above 153° C.

EXAMPLE 6

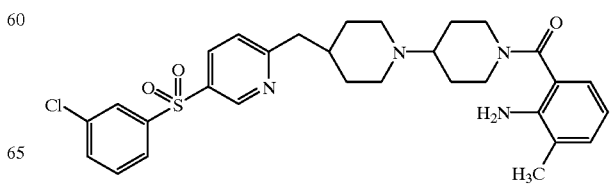

Step 1:

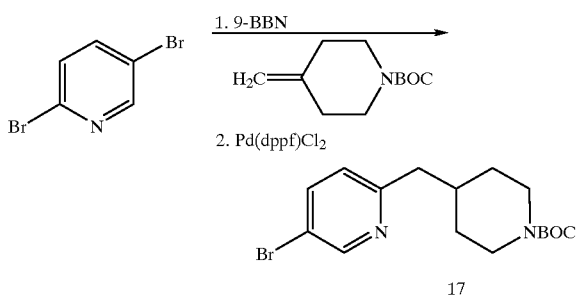

Treat 1 (7.93 ml) according to the procedure of Example 5, Step 3, using 9-BBN (92 ml), 2,5-dibromopyridine (10 g), DMF (95 ml), $H_2O$ (9.1 ml), $K_2CO_3$ (7.62 g) and Pd(dppf)$Cl_2$ (1.03 9). After purification, 17 was isolated as a solid (14.3 g) in 96% yield. mp: 66° C.

Step 2–3:

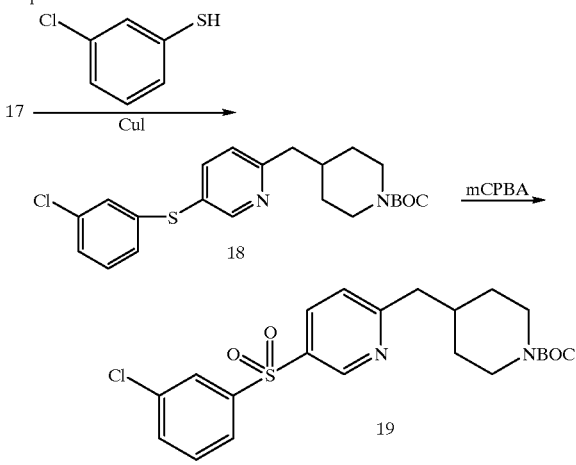

Step 2

NaH (1.01 g of a 60% dispersion in oil) was washed with hexane (6.0 ml). N,N-Dimethyl acetamide (8.4 ml) was added, the resulting mixture was cooled in an ice bath and 3-chlorothiophenol (2.94 ml) was added dropwise. After stirring at RT for 15 min, 17 (3.00 g) and CuI (4.82 g) were added all at once and the resulting mixture was heated at 120° C. for 12 h and then at 140° C. for 4 h. After cooling to RT, EtOAc (150 ml) was added, the mixture was filtered and rinsed with EtOAc. The combined EtOAc portions were washed with water and brine, dried over $MgSO_4$, filtered and evaporated to give a crude oil (4.77 9) which was further purified by column chromatography (silica adsorbent; 225 9; 1:8 EtOAc:hexanes; 1:4 EtOAc:hexanes; 1:2 EtOAc:hexanes eluant). After evaporation of the appropriate fractions, 18 (1.87 9) was isolated as a waxy solid in 53% yield.

Step 3

18 (1.00 9) was dissolved in $CH_2Cl_2$ (24 ml) and the resulting solution was cooled to 0° C., then mCPBA (1.21 g) was added over 10 min. The resulting mixture was stirred at RT for 24 h, diluted with $CH_2Cl_2$, made basic (pH=11) with 2N NaOH and the $CH_2Cl_2$ layer was removed. The organic layer was washed with water and brine, dried over $MgSO_4$, filtered and evaporated to give an oil (700 mg) which was further purified by column chromatography (silica adsorbent; 1:8 EtOAc:hexanes; 1:4 EtOAc:hexanes; 1:2 EtOAc:hexanes eluant). After evaporation of the appropriate fractions, 19 (196 mg) was isolated as a foam in 18% yield.

Step 4

19 (186 mg) was treated as in Example 1, Step 2, using $CH_2Cl_2$ (2.15 ml), TFA (0.43 ml) and $H_2O$ (7.8 EL). After work up, the desired amine was isolated as an oil (175 mg) which was used directly in the next step.

Step 5

The product of Step 4 (175 mg) was treated as in Example 1, Step 3, using N-tert-butoxy piperidone (399 mg), $CH_2Cl_2$ (2.5 ml), HOAC (29 µL) and NaB(OAc)$_3$H (148 mg). After work up and purification, the BOC-protected compound (67 mg) was isolated as a tan solid in 25% yield and was used directly in the next step.

Step 6

The product of Step 5 (67 mg) was treated as in Example 1, Step 2, using $CH_2Cl_2$ (3.0 ml), TFA (0.6 ml) and $H_2O$ (2.3 µL). After work up, the desired amine was isolated as an oil (42 mg) which was used directly in the next step.

Step 7

The product of Step 6 (21 mg) was treated as in Example 1, Step 5, using DMF (0.10 ml), HOBt (9 mg), iPr$_2$EtN (28 µL), 2-amino-3-methyl benzoic acid (11 mg) and DEC (12 mg). After work up and purification, the title compound (15 mg) was isolated in its free base form as a foam in 54% yield. HRMS: calc'd: M.H$^+$: $C_{30}H_{35}N_4O_3SCl$: 567.2197; measured: 567.2189.

Using a similar procedure, the following compound 6A was prepared:

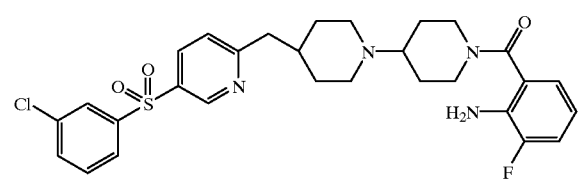

HRMS: calc'd: M.H$^+$: $C_{29}H_{33}N_4O_3SClF$: 571.1946; measured: 571.1939.

EXAMPLE 7

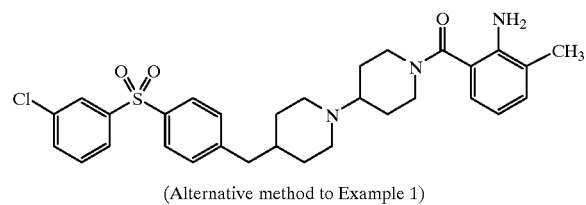

(Alternative method to Example 1)

Step 1:

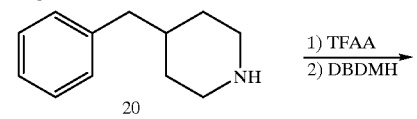

A solution of 20 (202 g, 1.15 moles) in $CH_2Cl_2$ (1.51) is treated with TFM (216 ml, 1.53 moles) added dropwise over the course of 30 min. The mixture is allowed to stir an additional 90 min at RT, then cooled to 0° C. in an ice bath.

To this is added CH$_3$SO$_3$H (306 ml) in portions followed by DBDMH (171 g, 0.6 moles) added in portions. The mixture is stirred overnight while coming to RT, then is cooled again in an ice bath. The reaction is quenched by addition of saturated aqueous Na$_2$S$_2$O$_3$ (1.8 ) added over 30 min. The aqueous layer is separated and washed with CH$_2$Cl$_2$ (2×2 1). The combined organic layers are dried over MgSO$_4$, filtered, and concentrated under vacuum. The residue is purified by chromatography over silica gel (2.5 kg), eluting with hexane (16 l), 5% EtOAc-hexane (16 1), and 10% EtOAc-hexane to yield 105 g of 21.

Steps 2–3:

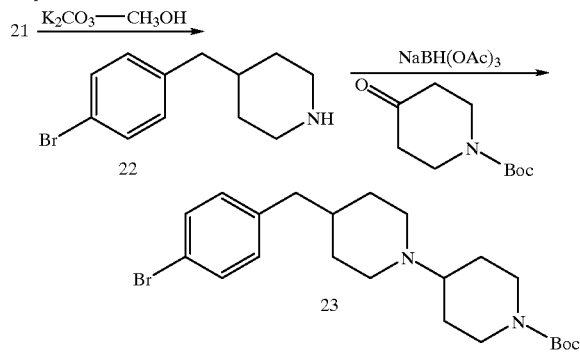

Step 2

A solution of the product of Step 1 (105 g) dissolved in CH$_3$OH (1.7 1) is treated with K$_2$CO$_3$ (90 g) and deionized water (300 ml). The mixture is stirred at RT for 3 , then concentrated under vacuum. The residue is treated with 2N NaOH (2 l) and extracted with CH$_2$Cl$_2$ (2×2 1). The combined organic layers are dried over MgSO$_4$, filtered, and evaporated to give 76 g of the desired product as an oil which partially crystallizes.

Step 3

A partial solution of the product of Step 2 in CH$_2$Cl$_2$ (1 l) is treated with N-t-butoxycarbonyl4-piperidone (64 g, 0.32 moles), glacial HOAc (38 ml), and NaBH(OAc)$_3$ (192.12 g, 0.9 moles). The mixture is allowed to stir overnight at RT, then poured into 2N NaOH (2 l). After stirring for 30 min, the layers are separated and the aqueous layer is extracted with EtOAc (2×2 l). The combined organic layers are dried over MgSO$_4$, filtered and evaporated. The residue is chromatographed over flash-grade silica gel (2 kg), eluting with EtOAc (40 1) to give 54.4 g of approx. 50% pure product followed by 30.2 g of pure product.

Step 4:

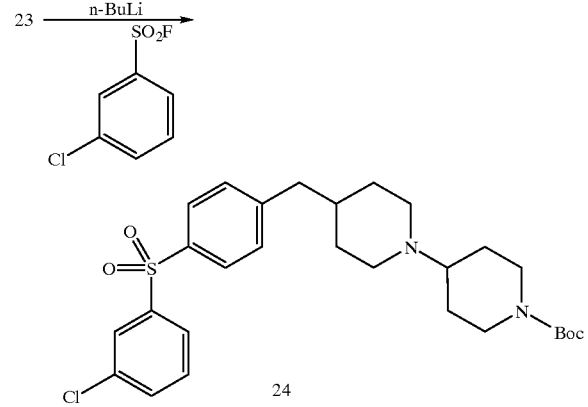

A solution of the product of Step 3 (8.8 g, 0.02 moles) in dry THF (35 ml) is cooled to −78° C. and treated with 2.5M n-BuLi in hexanes (8.05 ml, 0.02 moles) followed by a solution of 3-chlorobenzenesulfonyl fluoride (3.92 g, 0.02 moles) in THF (20 ml ). The mixture is stirred for 2 h at −78° C., then allowed to warm to RT overnight. The mixture is quenched with water and concentrated under vacuum. The residue is partitioned between EtOAc and 10% Na$_2$CO$_3$. The organic layer is washed with water, dried over MgSO$_4$, and evaporated. The residue is purified over silica gel, eluting with 5% CH$_3$OH-EtOAc. The purified residue is recrystallized from EtOAc to give 3.03 g of the desired product.

Steps 5–7

The product of step 4 was treated as in Example 1, Steps 4–6, to obtain the title compound.

Using a similar procedure, substituting the appropriate sulfonyl fluoride in step 4 and the appropriate carboxylic acid in step 5, compounds of the following formula were prepared

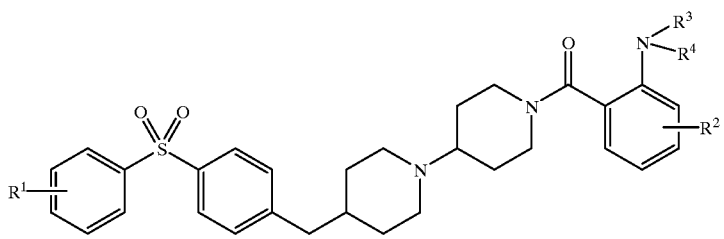
wherein the variables are as defined in the table:
| Ex. | R¹-phenyl | aniline group | Physical data |
|---|---|---|---|
| 7A | 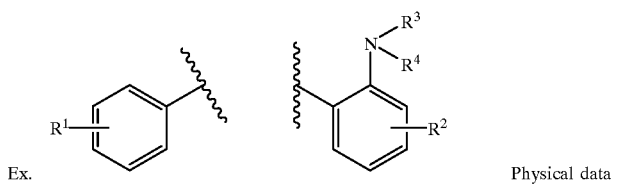 3-Cl | NH₂ (ortho) | HRMS found 552.1368 |
| 7B | 3-Cl | NHCH₃ (ortho) | HRMS found 566.1639 |
| 7C | 3-F | NH₂ (ortho) | HRMS found 535.6830 |
| 7D | 3-F | NHCH₃ (ortho) | HRMS found 549.7100 |
| 7E | 3-F | 2-NH₂, 6-CH₃ | HRMS found 549.7100 |
| 7F | 4-OCH₃ | NH₂ (ortho) | MS 548.1 (MH+) |

-continued

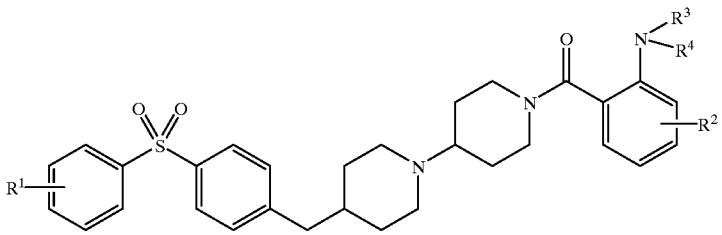

wherein the variables are as defined in the table:

| Ex. | <image cropped> | <image cropped> | Physical data |
|---|---|---|---|
| 7G | 3-Cl, 4-OCH₃ phenyl | 2-NH₂, 6-CH₃ phenyl | HRMS found 596.2362 |

What is claimed:

1. A compound having the structural formula

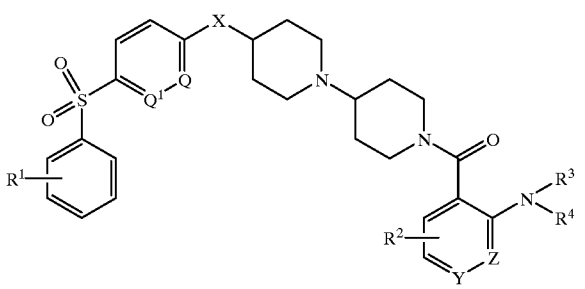

or a pharmaceutically acceptable salt, ester or solvate thereof, wherein

Q and $Q^1$ are each —CH=;

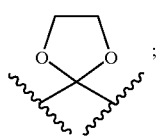

X is —CH$_2$— or

Y and Z are independently selected from the group consisting of —C(R$^5$)=, or one of Y and Z is —C(R$^5$)= and the other is —N=;

R$^1$ is 1 to 3 substituent independently selected from the group consisting of H, halogen and (C$_1$-C$_6$)alkoxy;

R$^2$ and R$^5$ are independently 1 to 3 substituents independently selected from the group consisting of H, halogen, (C$_1$-C$_6$)alkyl and (C$_1$-C$_6$)alkoxy; and R$^3$ and R$^4$ are independently selected from the group consisting of H and (C$_1$-C$_6$)alkyl.

2. A compound of claim 1 wherein Y and Z are both —C(R$^5$)=.

3. A compound of claim 2 wherein R$^5$ is H, methyl or halogen.

4. A compound of claim 1 wherein Y is =CH— and Z is —N=.

5. A compound of claim 4 wherein R$^2$ is H.

6. A compound of claim 1 wherein R$^1$ is halogen or methoxy.

7. A compound of claim 6 wherein R$^1$ is chloro.

8. A compound of claim 6 wherein R$^1$ is 3-chloro or 4-methoxy.

9. A compound of claim 1 wherein R$^2$ is Cl, F or methyl.

10. A compound of claim 9 wherein R$^2$ is 3-methyl.

11. A compound of claim 1 wherein R$^3$ and R$^4$ are each hydrogen.

12. A compound of claim 1 selected from the group consisting of compounds of the formula

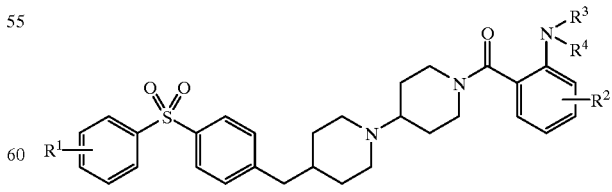

wherein the variables are as defined in the table:

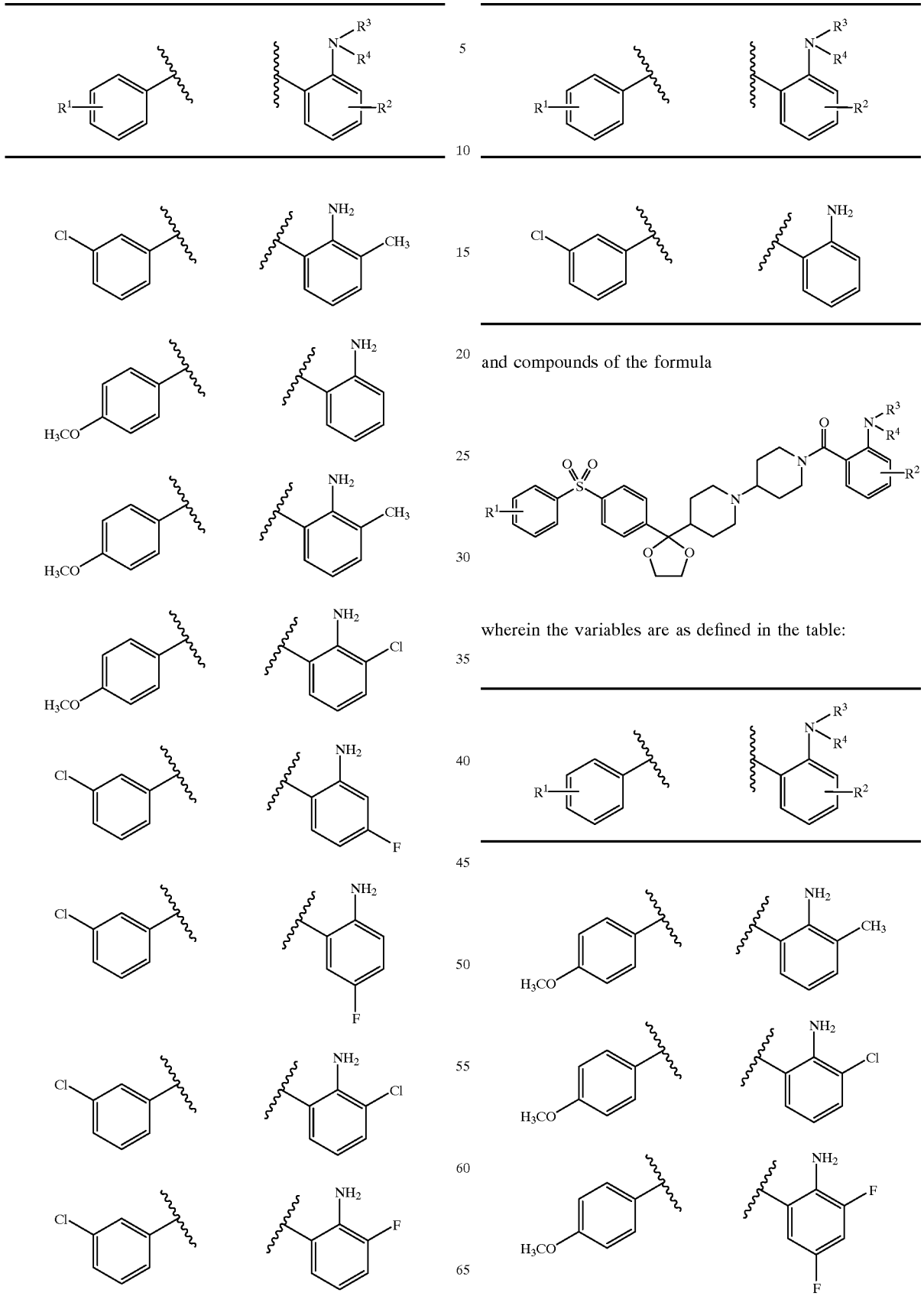

-continued

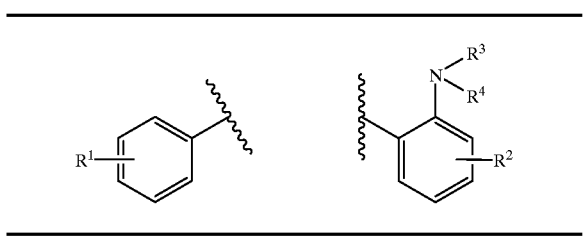

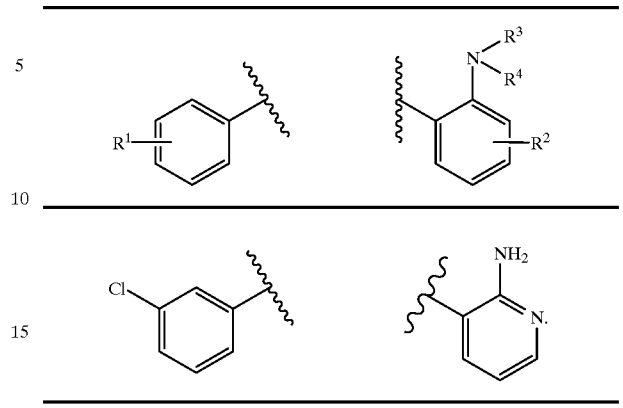

13. A pharmaceutical composition comprising a therapeutically effective amount of a compound of claim 1 in combination with a pharmaceutically acceptable carrier.

14. A method for treating a cognitive or neurodegenerative disease comprising administering to a patient suffering from said disease an effective amount of a compound of claim 1.

15. A method of treating a cognitive or neurodegenerative disease comprising administering to a patient suffering from said disease an effective amount of a combination of a compound of claim 1 with an acetylcholinesterase inhibitor.

16. A kit for treating a cognitive or neurodegenerative disease comprising in separate containers in a single package pharmaceutical compounds for use in combination, in one container a compound in accordance with claim 1 and in a separate container an acetylcholinesterase inhibitor, said compound and inhibitor each being in a pharmaceutically acceptable carrier and their combined quantities being an effective amount.

17.

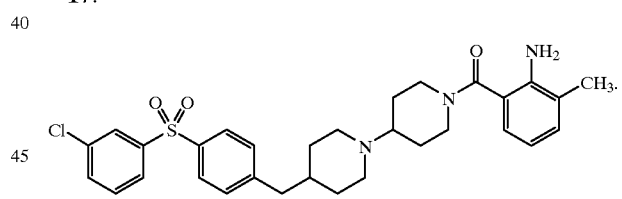

18.

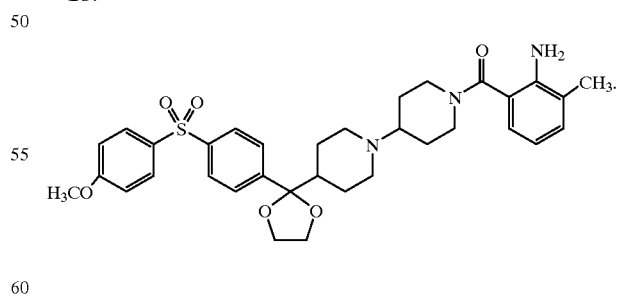

* * * * *